United States Patent
Chon et al.

(10) Patent No.: US 8,417,326 B2
(45) Date of Patent: Apr. 9, 2013

(54) RR INTERVAL MONITORING METHOD AND BLOOD PRESSURE CUFF UTILIZING SAME

(75) Inventors: Ki Chon, Mount Sinai, NY (US); Ernst A. Raeder, Setauket, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/671,847

(22) PCT Filed: Aug. 4, 2008

(86) PCT No.: PCT/US2008/072099
§ 371 (c)(1),
(2), (4) Date: Feb. 2, 2010

(87) PCT Pub. No.: WO2009/018570
PCT Pub. Date: Feb. 5, 2009

(65) Prior Publication Data
US 2011/0166466 A1  Jul. 7, 2011

Related U.S. Application Data

(60) Provisional application No. 60/953,508, filed on Aug. 2, 2007, provisional application No. 61/084,389, filed on Jul. 29, 2008.

(51) Int. Cl.
*A61B 5/046* (2006.01)
(52) U.S. Cl. ........ 600/518; 600/508; 600/509; 600/515; 600/516
(58) Field of Classification Search ............. 600/508, 600/509, 515, 516, 518, 519
See application file for complete search history.

(56) References Cited

U.S. PATENT DOCUMENTS

| | | | |
|---|---|---|---|
| 5,456,261 A | 10/1995 | Luczyk | |
| 5,522,396 A | 6/1996 | Langer et al. | |
| 5,622,178 A | 4/1997 | Gilham | |
| 5,868,680 A * | 2/1999 | Steiner et al. | 600/518 |
| 5,876,351 A | 3/1999 | Rohde | |
| 6,597,943 B2 * | 7/2003 | Taha et al. | 600/515 |
| 6,690,967 B2 | 2/2004 | Meij et al. | |
| 7,184,818 B2 | 2/2007 | Kim et al. | |
| 7,212,850 B2 | 5/2007 | Prystowsky et al. | |
| 7,273,454 B2 | 9/2007 | Raymond et al. | |
| 2005/0171447 A1 * | 8/2005 | Esperer | 600/515 |
| 2006/0084881 A1 | 4/2006 | Korzinov et al. | |
| 2006/0195037 A1 * | 8/2006 | Wiesel | 600/518 |
| 2006/0281999 A1 * | 12/2006 | Li | 600/518 |
| 2010/0056940 A1 * | 3/2010 | Moorman et al. | 600/518 |

FOREIGN PATENT DOCUMENTS

KR  10-2006-0134196 A  12/2006

OTHER PUBLICATIONS

Dash et al. "A Statistical Approach for Accurate Detection of Atrial Fibrillation and Flutter." Computers in Cardiology, 2009.*
Dash et al. "Automatic Real Time Detection of Atrial Fibrillation." Annals of Biomedical Engineering. Jun. 17, 2009.*

(Continued)

*Primary Examiner* — Carl H Layno
*Assistant Examiner* — Eugene Wu
(74) *Attorney, Agent, or Firm* — The Farrell Law Firm, P.C.

(57) ABSTRACT

Disclosed is an apparatus and method for ambulatory, real-time detection of Atrial Fibrillation (AF) providing an overall accuracy that refers to detection of AF, irrespective of the duration of AF and beat-to-beat classification.

15 Claims, 7 Drawing Sheets

OTHER PUBLICATIONS

The Diagnosis of Cardiac Arrhythmias: A Prospective Multi-Center . . . Rothman et al. Journal of Cardiovascular ElectroPhysiology vol. 18, No. 3, Mar. 2007, pp. 1-7.

RR Interval Dynamics Before Atrial Fibrillation in Patients After Coronary Artery Bypass Graft Surgery; Hogue et al.; Circulation, 1998; 98-429-134.

Monitor your heart health. Anytime. Anywhere; www.afibalert.com; 2008 (1page).

Ambulatory Cardiac Telemetry; www.cardguard.com; 2008 (5 pages).

CardioNet Study Facts; www.cardionet.com/medical_04.htm 2008 (2 pages).

Exponential Distribution of Long Heart Beat . . . Henning et al., Journal of Biological Physics, vol. 32. No. 5., Nov. 2006 (abstract).

Written Opinion of International Searching Authority, PCT/ISA/237 (3 pages), Feb. 13, 2009.

* cited by examiner

RR INTERVAL MONITORING METHOD AND BLOOD PRESSURE CUFF UTILIZING SAME

PRIORITY

This application claims priority to U.S. Provisional Application No. 60/953,508, filed Aug. 2, 2007, and to U.S. Provisional Application No. 61/084,389, filed Jul. 29, 2008, the contents of each of which is incorporated herein by reference.

BACKGROUND OF THE INVENTION

The present invention applies an algorithm for detection of Atrial Fibrillation (AF), which is one of the most common cardiac arrhythmias, afflicting approximately 2-3 million Americans. The incidence and prevalence of AF increase with age. With the graying of the baby boomers, it is estimated that 12-16 million individuals may be affected by 2050 and be at risk of significant mortality and morbidity from this arrhythmia.

AF has a prevalence of 17.8% and an incidence of 20.7/1,000 patient years in individuals older than 85. At age 55, the lifetime risk of developing AF is approximately 23%. AF is an independent risk factor for death (relative risk in men is 1.5 and in women 1.9). Furthermore, AF is a major cause of ischemic stroke, the impact of which increases with age and reaches 23.5% in patients older than 80. Accurate detection of AF is crucial since effective treatment modalities such as chronic anticoagulation and antiarrhythmic therapy, as well as radiofrequency ablation, are available but carry risks of serious complications. Despite the ubiquity of the arrhythmia, its diagnosis rests largely on the presence of symptoms and on serendipity. Unfortunately, since patients are often unaware of their irregular pulse, the diagnosis is often only established during a fortuitous doctor visit. If episodes of AF occur interspersed with normal sinus rhythm, the diagnosis presents an even greater challenge.

When AF is suspected, ambulatory monitoring can be performed in an attempt to document the arrhythmia. However, this approach is time consuming and not cost-effective for screening asymptomatic populations. Limitations of currently available technology including electrocardiography (for less than 10 seconds) and long-term monitoring. Ambulatory Holter monitoring is limited to no more than 48 hours and is cumbersome because it requires several leads connecting to a device worn on the patient's waist. After completion of the recording, the monitor is returned for data analysis by a cardiologist. Accordingly, real-time monitoring is not possible with conventional devices.

Conventional monitoring devices also include event monitors, which are small devices carried by a patient for up to 30 days. The patient will activate the event monitor upon when experiencing an irregular heart beat. A cardiologist will subsequently analyze recordings obtained by the event monitor.

For patients with very infrequent but potentially serious rhythm disturbances, an implantable loop recorder can be used. The implantable loop recorder continually records and overwrites the electrocardiogram for more than one year. When patients experience an event, they can freeze the recording and transmit the information to a cardiologist.

Several companies presently offer ambulatory heart monitors without AF detection capability. For example, CardioNet (www.cardionet.com) provides a 3-lead ECG monitor system which records and transmits data wirelessly to a hand held PDA for subsequent modem or Internet transmission. See, Rothman, et al., *Diagnosis of Cardiac Arrhythmias* Journal of Cardiovascular Electrophysiology, Vol. 18, No. 3, March 2007, U.S. Pat. No. 7,212,850 and Patent Appl. Pub No. U.S. 2006/0084881 A1 of Korzinov et al., the contents of which are incorporated herein by reference.

Conventional systems also include wireless transmission of ECG data, as discussed in U.S. Pat. No. 5,522,396, a 12-lead Holter ECG system, as discussed in U.S. Pat. No. 6,690,967, and an event recorder system, as discussed in U.S. Pat. No. 5,876,351, the contents of each of which are incorporated herein by reference.

An AfibAlert device, see www.afibalert.com, monitors for AF during a 45-second testing period. However, the AfibAlert device does not provide a continuous or real-time detection and monitoring of the heart, and therefore cannot alert if AF happens at any other time. In addition, the cost of the AfibAlert device is relatively high for wide acceptance by the general population. Furthermore, the 90-93% accuracy of the AfibAlert device is below the accuracy of the detection algorithm of the present invention.

A number of algorithms have been developed to detect AF. Such conventional algorithms can be categorized based on P-wave detection and RR interval (RRI) variability (HRV). Since there is no uniform depolarization of the atria during AF, there is no discernible P-wave in the ECG. This fact has been utilized in detection of AF by trying to identify whether the P-wave is absent. However, in most cases the location of the P-wave fiducial point is very difficult to find. Moreover, the P-wave may be small enough to be corrupted by noise that is inherent in surface measurements. The methods in the second category do not require identification of the P-wave and are based on the variability of RRI series. However, few algorithms in this category show high predictive value for clinical application. A notable exception is discussed by Duverney et al. in *High Accuracy of Automatic Detection of Atrial Fibrillation using Wavelet Transform of Heart Rate Intervals*, Pacing Clin Electrophysiol 25: 457-462, 2002, and by Tateno et al. in *Automatic Detection of Atrial Fibrillation using the Coefficient of Variation and Density Histograms of RR and delta RR Intervals*, Medical & Biological Engineering & Computing 39: 664-671, 2001.

Duverney et al. use wavelet transform of the RRI time series where the sensitivity and specificity was 96.1% and 92.6% for AF beats, respectively, on a European database consisting of 15 subjects. Tateno et al. compare the density histogram of a test RRI (and $\Delta$RRI) segment with previously compiled standard density histograms of RR (and $\Delta$RR) segments during AF using the Kolmogorov-Smirnov test, to report a sensitivity of 94.4% and specificity of 97.2% for AF beats for the MIT BIH Atrial Fibrillation database. However, the accuracy of the Tateno et al. algorithm relies on the robustness of training data and that their results were based on a limited database. However, in most clinical applications, it may be difficult to obtain such large databases of training data.

In view of a general consideration of AF as being a random sequence of heart beat intervals with markedly increased beat-to-beat variability, the present invention combines four statistical techniques to exploit a Root Mean Square of Successive RR interval differences to quantify variability (RMSSD), a Turning Points Ratio to test for randomness of the time series (TPR), a Shannon Entropy (SE) to characterize its complexity and a autocorrelation (ACORR) index to characterize correlation between the first two RR intervals. In contrast to the Tateno-Glass method, the algorithm of the present invention does not require training data. See, Lu S, Chon K H, and Raeder E, *Automatic Real Time Detection of Atrial Fibrillation*, Heart Rhythm 4: S36, 2007.

The present invention provides a method and apparatus for utilizing an algorithm that accurately detects, in a real-time manner, the presence of AF utilizing piezoelectric or ECG signals. The present invention also provides a portable blood pressure cuff, for home monitoring.

SUMMARY OF THE INVENTION

The present invention provides a real-time AF analysis by obtaining a patient heartbeat; analyzing select consecutive obtained heartbeats; selecting a beat segment of RR intervals centered on that beat for each analyzed heartbeat; eliminating ectopic beats and compensatory pause associated with each ectopic beat; calculating a root mean square of successive RR differences (RMSSD) of the beat segment; and performing a first identification that the beat segment is an AF candidate by determining whether the RMSSD is greater than a RMSSD threshold.

In a preferred embodiment of the presenting invention, if an AF candidate identification is made, a second identification is performed of the beat segment by calculating a Turning Points Ratio (TPR) of the segment and determining whether the TPR satisfies randomness criteria. If it is again identified as an AF candidate, a third identification of the beat segment is performed by calculating a Shannon Entropy (SE) of the segment and determining whether the SE is greater than an SE threshold.

BRIEF DESCRIPTION OF THE DRAWINGS

The above and other objects, features and advantages of certain exemplary embodiments of the present invention will be more apparent from the following detailed description taken in conjunction with the accompanying drawings, in which.

DETAILED DESCRIPTION OF THE PREFERRED EMBODIMENTS

The following detailed description of preferred embodiments of the invention will be made in reference to the accompanying drawings. In describing the invention, explanation about related functions or constructions known in the art are omitted for the sake of clearness in understanding the concept of the invention, to avoid obscuring the invention with unnecessary detail.

A preferred embodiment of the present invention utilizes a Turning Points Ratio (TPR) to determine whether an RR interval sequence is random, for application of the TPR non-parametric statistical test comparing each point in the time series to neighboring points.

FIG. 1 shows, in panel (a), an original heart beat interval time series from a section of file 5162 of a MIT BIH Atrial Fibrillation database. FIG. 1 also shows calculation of the RMSSD, TPR, Shannon Entropy and ACORR, in panels (b)-(e) respectively, for the same segment is shown. Panel (f) of FIG. 1 shows final detection results based on whether the above statistics cross respective thresholds that are shown in dashed lines for panels (b)-(e).

Panel (a) of FIG. 1 shows a long-term recording with an episode of AF embedded in normal sinus rhythm in which random behavior of AF is clearly observed. As shown in Panels (b) through 1(f) of FIG. 1, the combination of TPR, RMSSD, SE and ACORR greatly enhances the accuracy of AF detection.

In a computer generated random time series, the probability of an interval being surrounded by either two higher or two lower intervals ("Turning Point") is equal to $\frac{2}{3}$. Given three random numbers $a_1$, $a_2$, $a_3$ where $a_1 > a_2 > a_3$, there are six combinations to generate a series. Among them, $(a_1 a_3 a_2)$, $(a_2 a_3 a_1)$, $(a_2 a_1 a_3)$ and $(a_3 a_1 a_2)$ include turning points while $(a_1 a_2 a_3)$ and $(a_3 a_2 a_1)$ do not. Given a random series of length n, the expected number of turning points is $$\frac{2n-4}{3},$$

and the standard deviation is $$\sqrt{\frac{16n-29}{90}}.$$

Hence, the expected Turning Points Ratio (TPR) of a random series is provided in Equation (1):

$$TPR = \frac{2n-4}{3n} \pm \sqrt{\frac{16n-29}{90}} \quad (1)$$

Confidence limits of this ratio are defined to estimate randomness boundaries in a time series. A series with ratios below the lower 95% confidence interval exhibits periodicity (e.g. sinus rhythm) whereas TPRs above the upper 95% confidence limit approaching 1.0 are evidence of alternans where ultimately every point is a turning point ("ABABAB" pattern).

Figure 1A:
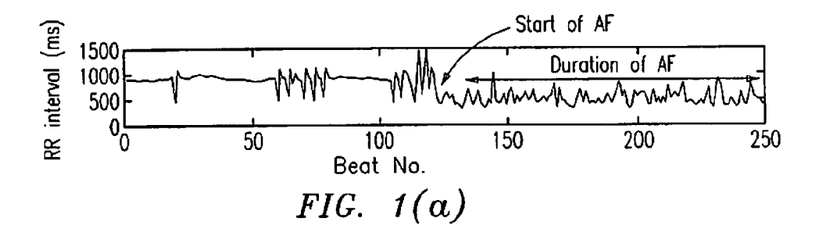
FIG. 1 is a chart showing threshold values for AF detection.
Figure 1B:
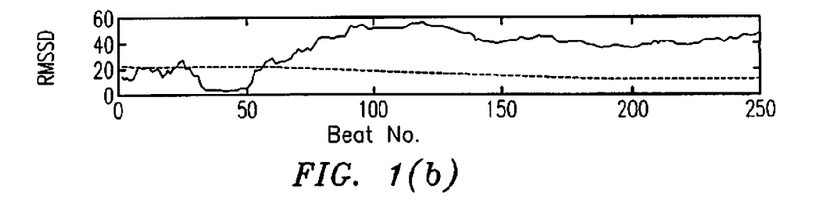
Figure 1C:
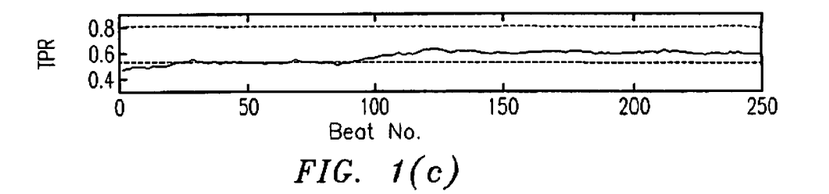
Figure 1D:
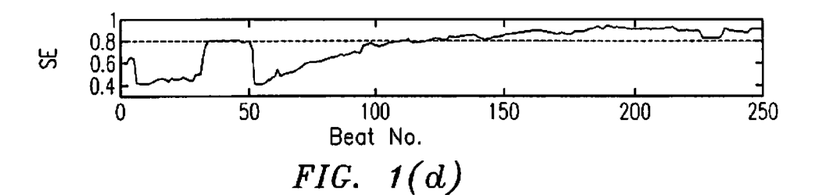
Figure 1E:
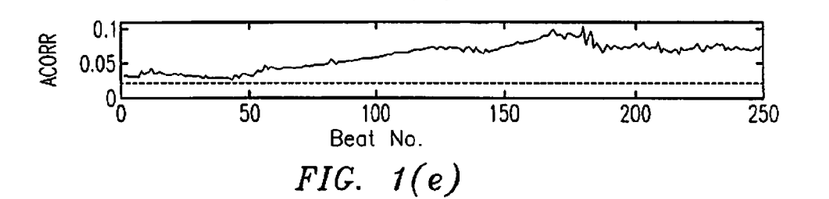
Figure 1F:
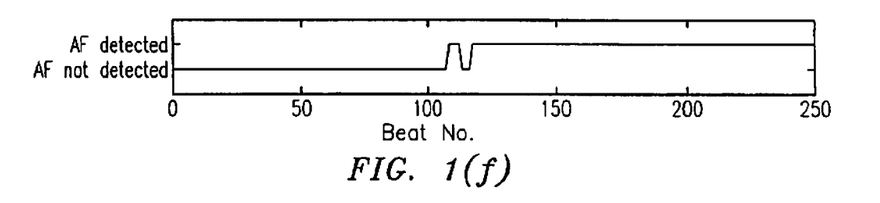
Figure 2:
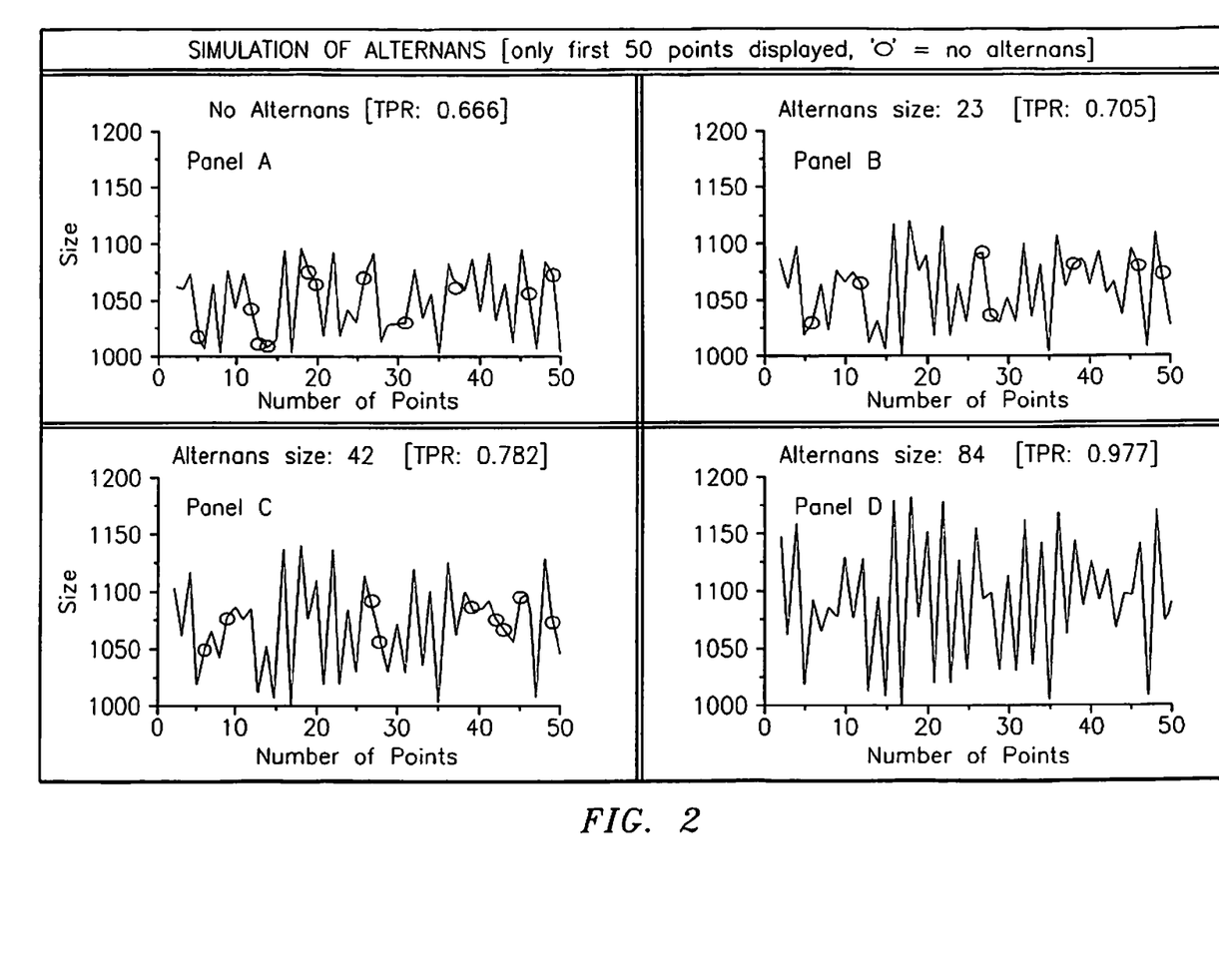
FIG. 2 depicts random numbers subjected to turning points analysis.
Figure 3A:
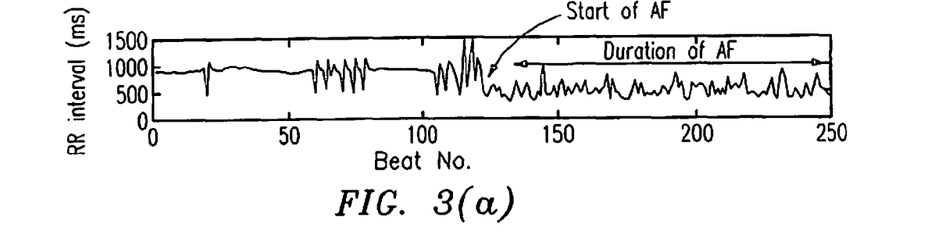
FIG. 3 shows an AF episode, including RMSSD, TPR, Shannon Entropy and ACORR.
Figure 3B:
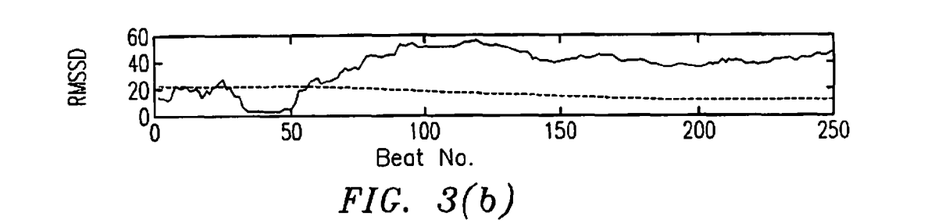
Figure 3C:
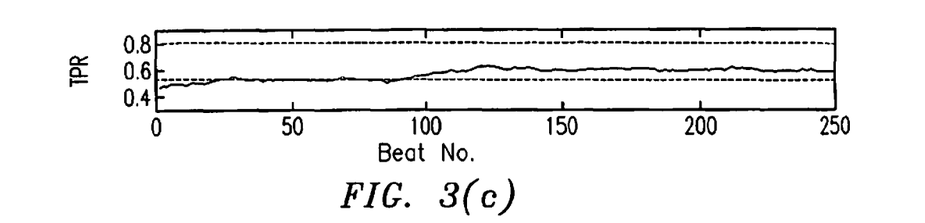
Figure 3D:
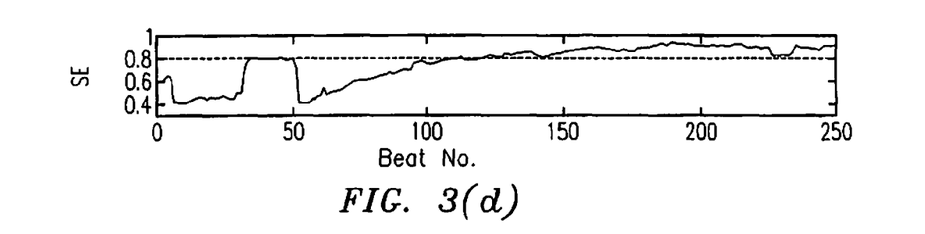
Figure 3E:
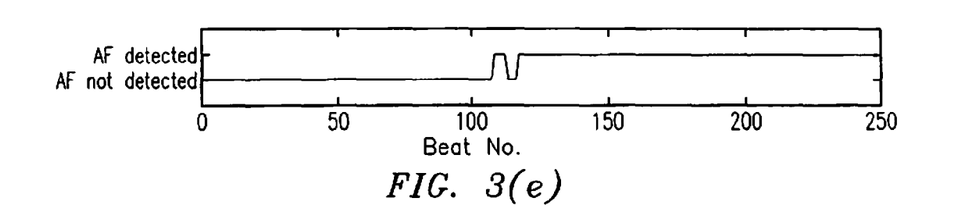

FIG. 2 shows an analysis of one thousand (1000) random numbers subjected to turning points analysis. As expected, Panel A shows the TPR of the random number sequence is $\sim\frac{2}{3}$. When increasing levels of alternans are imposed, as shown in Panels B through D of FIG. 2, the TPR increases above the 95% confidence limit for randomness until approaching unity.

In the present invention, a Root Mean Square of Successive Differences is preferably performed as a second component of the algorithm. In the present invention, beat-to-beat variability is estimated by the root mean square of successive RR differences (RMSSD). Since AF exhibits higher variability between adjacent RR intervals than periodic rhythms such as sinus rhythm, the RMSSD is expected to be higher. For a given segment a(i) of RR intervals of some length l, the RMSSD is given by Equation (2):

$$RMSSD = \sqrt{\frac{1}{128} \sum_{j}^{j+l=1} (a(j+1) - a(j))^2} \quad (2)$$

A third component of the algorithm of the present invention is Shannon Entropy (SE), which provides quantitative information about the complexity of a signal. Complexity refers to the difficulty in describing or understanding a signal. For example, signals with discernible regular patterns are easier to describe than signals with a higher degree of irregularity. The SE quantifies how likely runs of patterns that exhibit regularity over a certain duration of data also exhibit similar regular patterns over the next incremental duration of data. For example, a random white noise signal is expected to have the highest SE value (1.0) whereas a simple sinusoidal signal will have a very low SE (~0.2) value. Thus, the SE values of normal sinus rhythm and AF can be expected to differ significantly.

Calculation of SE of the RR interval time series is performed by first constructing a histogram of the segment considered. The eight maximum and eight minimum RR values in the segment are considered outliers and are removed from consideration. The remaining RR intervals are sorted into equally spaced bins whose limits are defined by the minimum and maximum RR interval after removing outliers. To obtain a reasonably accurate measure of the SE, at least 16 such bins are needed. Based on an ROC curve analysis, the segment length for AF detection was set at 128 beats.

An estimation of probability is performed as a next step in the calculation of SE, preferably by computing for each bin as the number of beats in that bin divided by the total number of beats in the segment (after removing outliers), for example see Equation (3):

$$p(i) = \frac{No\,of\,beats\,in\,bin(i)}{Total\,number\,of\,beats\,in\,the\,segment} = \frac{No\,of\,beats\,in\,bin(i)}{128 - 16} = \frac{No\,of\,beats\,in\,bin(i)}{112} \quad (3)$$

The SE is then calculated utilizing Equation (4):

$$SE = -\sum_{i=1}^{16} p(i) \frac{\log(p(i))}{\log\left(\frac{1}{16}\right)} \quad (4)$$

The autocorrelation function is also used to characterize correlation between current and past samples of RR intervals. A practical estimate is provided by Equation (5).

$$\varphi_{xx}(\tau) = \frac{1}{R - \tau} \int_0^{\tau} x(t) x(t - \tau) dt \quad (5)$$

Thus, $\phi_{xx}(\tau)$ is a measure of how correlated x(t) is with its past value τ seconds earlier. Obviously, for noisy or broadband data, the autocorrelation at all delays other than 0 will be close to 0. This fact is utilized for the detection of AF from its RR interval series by taking the difference between the autocorrelation at delay 0 and at delay 1 and comparing with some threshold. In addition, the autocorrelation at delay 0 is always normalized to 1 so as to enable comparison with a fixed and easy-to-compute threshold. A threshold of 0.02 was used for ACORR, that is any value that is greater than 0.02 is considered as AF.

In the present invention, a filtering of ectopic beats is preferably also performed. Ectopic beats occurring during regular sinus rhythm are a potential cause of erroneous detection of AF since they confound all three components of the algorithm. Typically, a premature beat is characterized by the combination of a short coupling interval to the preceding normal RR interval, followed by a compensatory pause which is longer than both the ectopic coupling interval and the subsequent normal RR interval.

Thus, if the i-th RR interval is premature and the i-th+1 RR the compensatory pause, then RR[i−1]>RR[i]<RR[i+1] and RR[i]<RR[i+1]>RR[i+2], yielding at least two additional turning points and three if RR[i+1]>RR[i+2]<RR[i+3]. In order to recognize the characteristic short-long RR interval sequence of ectopic beats a ratio RR[i]/RR[i−1] is computed for each RR interval in the time series. For a regular sinus rhythm, this ratio is close to unity and fluctuations around it represent physiologic variability. In the case of ectopy, the sequence of ratios is RR[i]/RR[i−1]≦0.8, RR[i+1]/RR[i]≧1.3, and RR[i+2]/RR[i+1]≦0.9. Preferably, rather than relying on an arbitrary fixed ratio, diverse ectopic beats with varying coupling intervals are captured by searching for RR sequences which satisfy the conditions RR[i]/RR[i−1]<Perc1 and RR[i+1]/RR[i]>Perc99 and RR[i+1]/RR[i+2]>Perc25 (where Perc1, Perc99, and Perc25 are the first, 99th, and 25th percentile of RR ratios, respectively). When an ectopic beat is encountered, it is excluded from further analysis along with its compensatory pause.

The present invention utilizes the following threshold definitions. Optimal cut-points for the algorithm of the present invention are identified by plotting the ROC for RMSSD, selecting a threshold that optimizes sensitivity so that a maximum number of possible AF beats can pass through to the next step. Such threshold definition minimizes the likelihood that true AF beats are filtered out in the first step of the analysis cascade.

In a preferred embodiment, a threshold of 9.8% of the mean RR interval of the 128-beat segment was used, based on inspection of the ROC, to yield a sensitivity and specificity of 99.1% and 79.33% for AF beats, respectively.

Next, keeping the RMSSD threshold fixed, a Turning Points analysis was added and a second ROC was constructed by varying only the confidence interval of the expected turning points ratio. As discussed above, the expected TPR of a random series is 0.666±confidence interval. The ROC is obtained by varying the confidence interval of the TPR and plotting the corresponding sensitivity against the specificity. Again, the TPR threshold is selected so as to maximize the sensitivity without compromising on the specificity (e.g. this resulted in the sensitivity and specificity of 97.06% and 86.47% for AF beats, respectively).

Based on this analysis, sensitivity and specificity for AF detection are optimal for a confidence interval of the TPR between 0.527 and 0.8. Using the same approach for SE reveals the optimal cut point to be 0.8. For the AFIB database (N=23 subjects), a threshold of 0.8 for the SE gave a sensitivity of 95.06% and specificity of 96.68% of all AF beats. Using the same criteria on the 200 series of the MIT BIH Arrhythmia database (N=25 subjects) gave a sensitivity of 88.13% and a specificity of 82.01% for AF beats. For the 100 series in the same database (N=23 subjects), the specificity was 98.38% for AF beats. Since there are no true AF beats in this series, the sensitivity cannot be quantified.

Testing was performed utilizing a 200 series of a MIT BIH Arrhythmia database (N=25 subjects), which is the most challenging database because it contains many artifacts, including Atrial Premature Beats (APB), Ventricular Premature Beats (VPB). Removal of VPB prior to data analysis was found to increase sensitivity and specificity on the 200 series of the MIT BIH Arrhythmia database to 88.24% and 88.01% for AF beats, respectively.

For clinical applications, a most relevant objective is detection of AF in a given recording, not necessarily every single AF beat. Using this criterion, a sensitivity of 100% was achieved for both the AF and arrhythmia databases. The results of use of the present invention are summarized in Table 1, which provides AF detection accuracy.

TABLE 1

| Database | AF beats (Sensitivity %/ Specificity %) | AF episodes (Sensitivity %/ Specificity %) |
|---|---|---|
| MIT-BIH AFIB (N = 23) | 93.51/97.03 | 100/99.11 |
| MIT-BIH Arrhythmia 100 series (N = 23) | NA/98.38 (note: no AF in this database) | NA |
| MIT-BIH Arrhythmia 200 series (N = 25) | 88.24/88.01 | 100/100 |
| ScottCare Holter (N = 23) | Not available | 100/96 |

Furthermore, automatic real time detection of AF in a clinical setting appears feasible with the combined use of TPR, RMSSD and SE, as the algorithm takes only 2.5 seconds to compute 24-hour Halter data which contains approximately 100,000 beats. The only requirement of our algorithm is that at least 1.5-2 minutes of RR interval data are needed since the SE test requires 128 beats. The computation time of a 128-beat data segment is on the order of 1-2 milliseconds.

FIG. 1 provides an example calculation of these statistics, along with the final detection using the corresponding thresholds for a sample recording from the MIT BIH Atrial Fibrillation database. FIG. 1(a) shows an episode of AF embedded in Sinus Rhythm from the MIT-BIH Atrial Fibrillation database is shown, FIG. 1(b) shows an RMSSD, FIG. 1(c) shows a TPR, FIG. 1(d) shows SE, and FIG. 1(e) shows ACORR. Dotted lines in (b-e) represent threshold values as determined by the ROC. A final detection result as to whether an AF is detected is displayed in (f).

A recent analysis of 23 Holter recordings as provided by ScottCare Corporation, correct identification was made the presence of AF episodes in all subjects (sensitivity of 100% and specificity of 96%).

In another preferred embodiment of the present invention, a piezoelectric sensor is utilized to obtain RR intervals. This will facilitate a shift from current clinical practice of centralized AF detection (i.e. making the diagnosis at a doctor's office, clinic or hospital) to a distributed model relying on the patients themselves to obtain the data. The present invention "piggy-backs" on daily blood pressure checks made at home, in a pharmacy, or even in select stores. In the preferred embodiment, a signal is acquired through a blood pressure cuff adapted with an embedded piezoelectric sensor, to obviate the need for an electrocardiogram.

Figure 4:
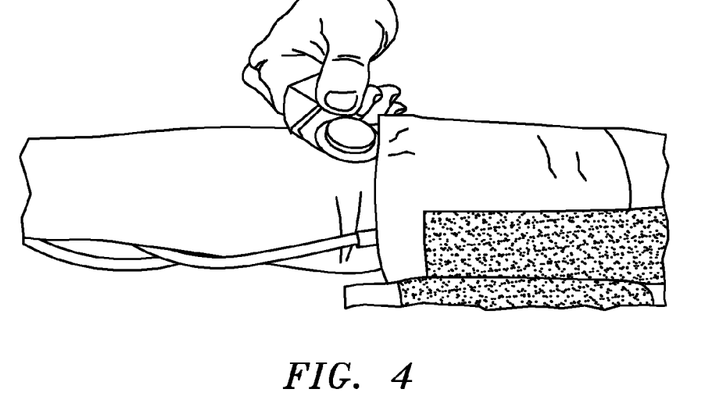
FIG. 4 shows a piezoelectric sensor incorporated in a blood pressure cuff.
Figure 5:
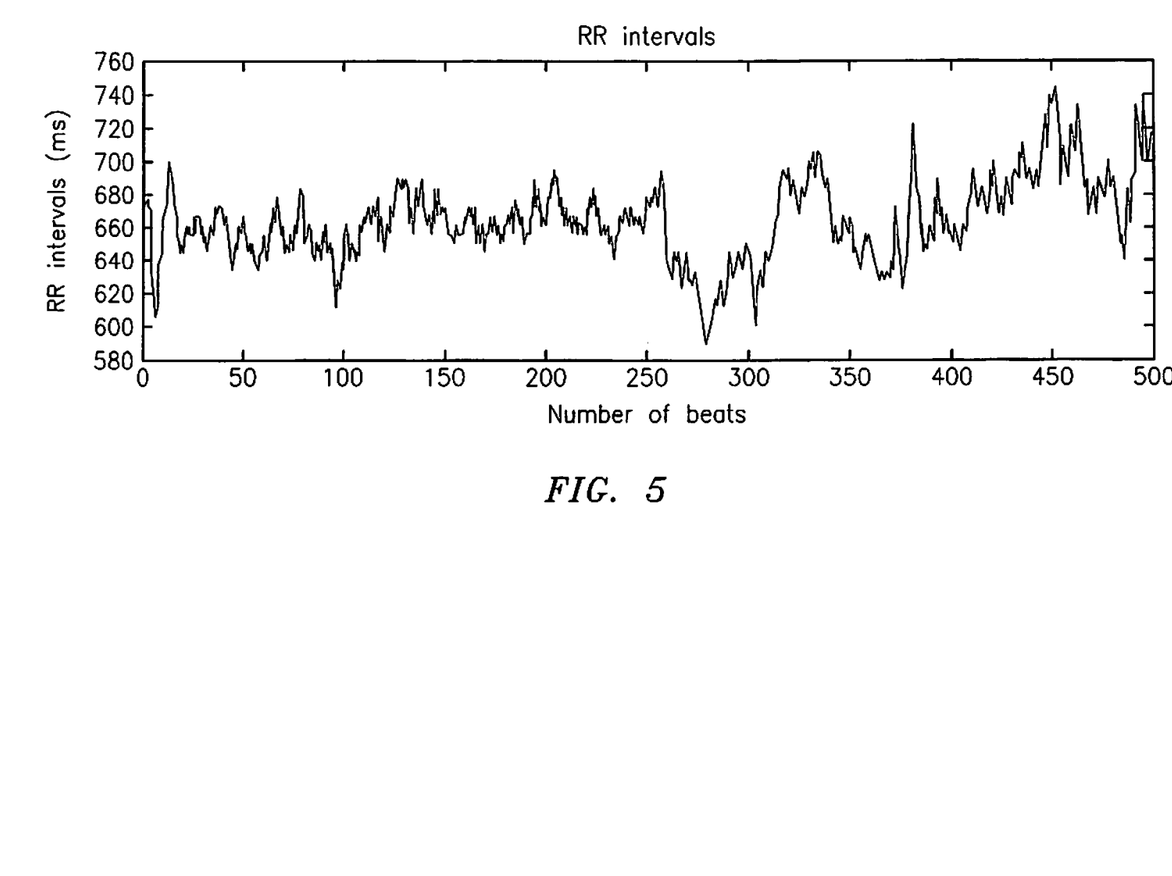
FIG. 5 provides a comparison of RR intervals obtained from a commercial ECG device and PPV values obtained utilizing the piezoelectric sensor of the present invention.

FIG. 4 shows a piezoelectric sensor incorporated into a blood pressure cuff for placement on a finger or on the brachial artery, and FIG. 5 provides a comparison of RR intervals obtained from a commercial ECG device and PPV obtained via a piezoelectric sensor.

A preferred embodiment of the present invention embeds a piezoelectric crystal in a blood pressure cuff, as shown in FIG. 4. A signal from the piezoelectric crystal is utilized to obtain statistical criteria to diagnosis/exclude AF. In the preferred embodiment, a peak systolic blood pressure is derived from successive heart beats. The preferred embodiment allows for remote patient monitoring in an essentially burden-free manner. The preferred embodiment allows diagnosis to be made of asymptomatic patients that is not addressed in conventional systems.

As shown in FIG. 5, a close correlation exists between ECG and piezoelectric sensor derived signals. The device of the present invention does not impose an additional burden on the patient, other than an additional 3-5 minute data collection period. Moreover, since recording of an electrocardiogram with its attendant cost is avoided, since the piezoelectric sensor is reusable and does not require separate energy source, the incremental cost is minuscule compared to the potential public health benefit.

Figure 6A:
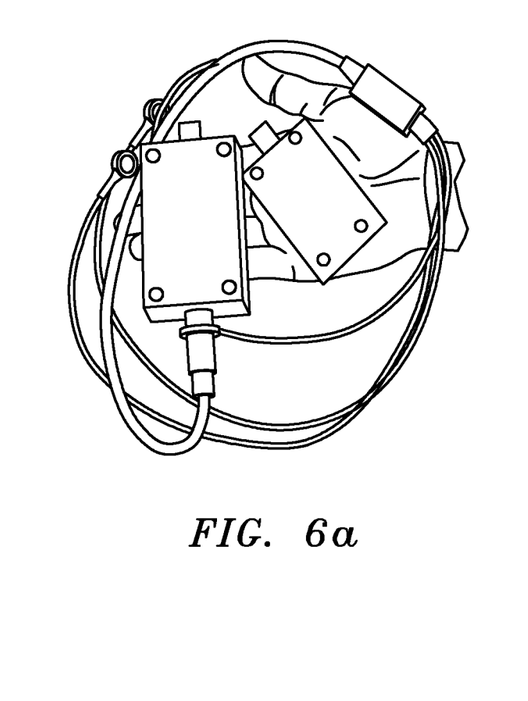
FIGS. 6(a) and 6(b) shows an integrated wireless ECG device and wireless ECG collection of the present invention.
Figure 6B:
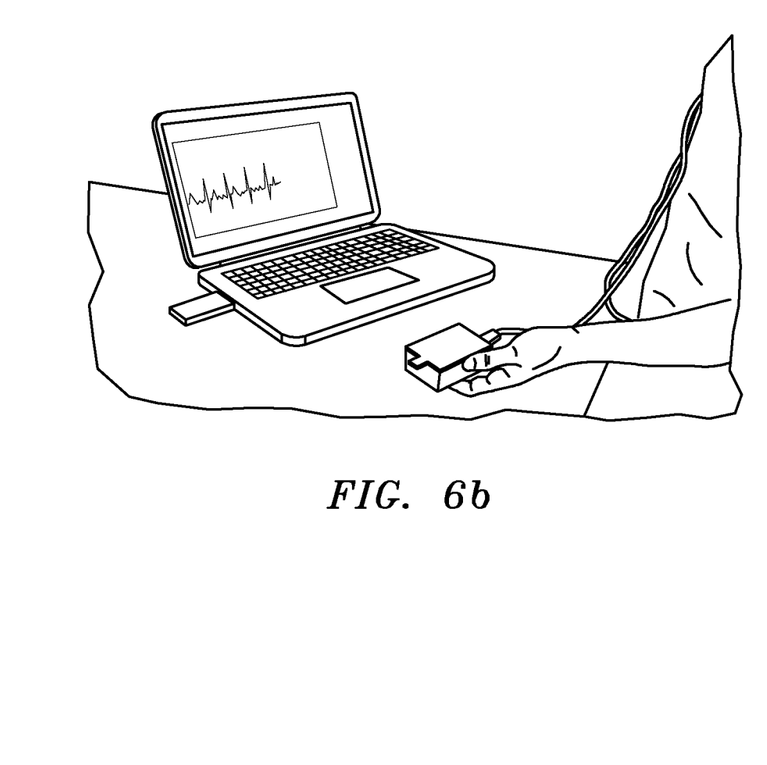
Figure 7:
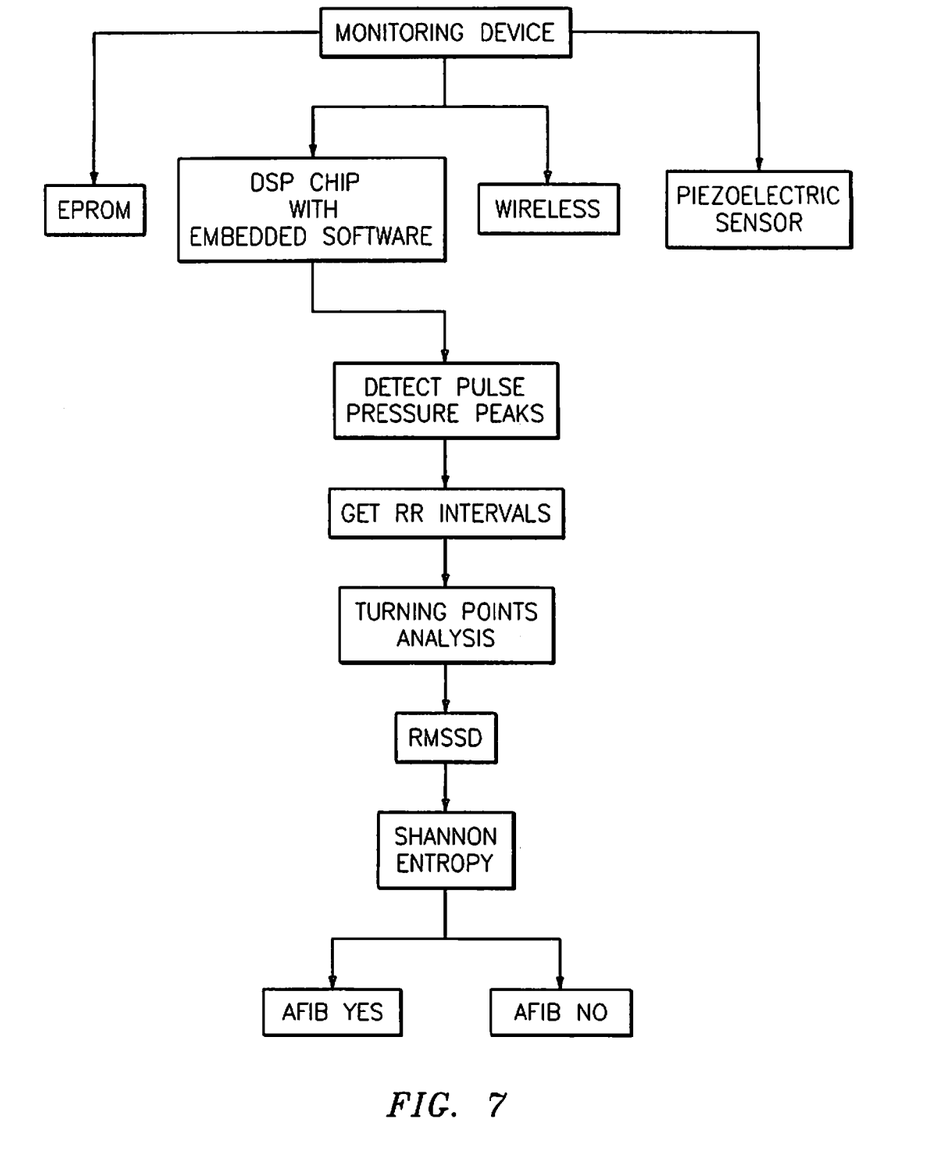
FIG. 7 is a flowchart showing operation of a preferred embodiment of the present invention.

FIG. 6(a) shows a prototype of a wireless two-channel ECG circuit and FIG. 6(b) shows wireless data collection of ECG developed in accordance with the present invention. FIG. 7 provides a flowchart summarizing data acquisition and the analysis algorithm.

While the invention has been shown and described with reference to certain exemplary embodiments of the present invention thereof, it will be understood by those skilled in the art that various changes in form and details may be made therein without departing from the spirit and scope of the present invention as defined by the appended claims and equivalents thereof.

What is claimed is:

1. An Atrial Fibrillation (AF) analysis method comprising:
   obtaining an output that includes a heart beat;
   deriving a heart beat interval;
   analyzing a number (N) of heart beat intervals from the output; and
   detecting a likelihood of AF by:
      calculating a Turning Points Ratio (TPR) of the N heart beat intervals;
      calculating a root mean square of successive (RMSSD) heart beat intervals; and
      calculating Shannon Entropy (SE) of the N heart beat intervals.

2. The method of claim 1, further comprising determining whether the RMSSD is greater than a RMSSD threshold.

3. The method of claim 2, wherein the RMSSD threshold is a percentage of a mean heart beat interval of a beat segment of the N intervals.

4. The method of claim 1, further comprising determining whether the SE is greater than an SE threshold.

5. The method of claim 1, further comprising determining if the calculated TPR meets a randomness criteria.

6. The method of claim 1, further comprising:
   calculating autocorrelation coefficients at time delays (a) and (b);
   determining a difference there between and comparing the difference to a threshold; and
   detecting an AF upon finding the difference to exceed the threshold, thereby obtaining improved specificity and sensitivity of AF identification.

7. The method of claim 6, wherein time delay a=0 interval and b=1 interval and the autocorrelation coefficients at delay 0 are normalized to 1.

8. The method of claim 7, wherein the analysis is repeated until the end of the output is reached.

9. The method of claim 1, wherein calculation of the TPR, of the RMSSD, and of the SE is performed in varied order.

10. The method of claim 1, further comprising elimination of ectopic beats and a plurality of compensatory pauses.

11. The method of claim 10, wherein the plurality of compensatory pauses are associated with each ectopic beat.

12. The method of claim 1, wherein the heart beat interval is derived between select peaks in the output.

13. The method of claim 1, wherein the output is obtained from one of an ECG, a piezoelectric sensor, continuous blood pressure monitoring and pulse oximeter data.

14. The method of claim 1, wherein the output is obtained in real time.

15. An apparatus for Atrial Fibrillation (AF) detection, the apparatus comprising:
- a sensor for obtaining an output that includes a heart beat; and
- a processor for deriving a heart beat interval from the output, and analyzing a number (N) of heart beat intervals from the output, wherein the processor is configured to detect a likelihood of AF by:
    - calculating a Turning Points Ratio (TPR) of the N heart beat intervals,
    - calculating a root mean square of successive (RMSSD) heart beat intervals, and
    - calculating Shannon Entropy (SE) of the N heart beat intervals.

\* \* \* \* \*